US00PP20255P2

(12) United States Plant Patent
van Dijk

(10) Patent No.: US PP20,255 P2
(45) Date of Patent: Sep. 1, 2009

(54) ***ANTHURIUM* PLANT NAMED 'ANTHCIMWI'**

(50) Latin Name: *Anthurium andreanum*
Varietal Denomination: Anthcimwi

(75) Inventor: Jan van Dijk, Bleiswijk (NL)

(73) Assignee: Anthura B.V., Bleiswijk (NL)

( * ) Notice: Subject to any disclaimer, the term of this patent is extended or adjusted under 35 U.S.C. 154(b) by 0 days.

(21) Appl. No.: 12/157,557

(22) Filed: Jun. 11, 2008

(51) Int. Cl.
*A01H 5/00* (2006.01)

(52) U.S. Cl. ..... Plt./365; Plt./369

(58) Field of Classification Search ..... Plt./365, Plt./369
See application file for complete search history.

(56) References Cited

PUBLICATIONS

UPOV–ROM PBR 20052682, published Feb. 15, 2006.*

* cited by examiner

*Primary Examiner*—Bruce Campbell
*Assistant Examiner*—Louanne C Krawczewicz Myers
(74) *Attorney, Agent, or Firm*—Jondle & Associates, P.C.

(57) ABSTRACT

A new *Anthurium* plant particularly distinguished by having unique brown-red, durable spathes, dark-green, compact, durable leaves, a medium-long erect penduncle, rich shoot formation, flowers early and continuously throughout the year, a compact and full plant habit and a plant height of 30 cm to 35 cm, is disclosed.

2 Drawing Sheets

Genus and species: *Anthurium andreanum* L.
Variety denomination: 'Anthcimwi'.

BACKGROUND OF THE NEW PLANT

The present invention comprises a new and distinct cultivar of *Anthurium,* botanically known as *Anthurium andreanum* L., and hereinafter referred to by the cultivar name 'Anthcimwi'. The new cultivar originated from a hybridization made in 2000 in Bleiswijk, The Netherlands. The female parent was a red *Anthurium* pot plant '00-2935-05' (unpatented), while the male parent was a brown *Anthurium* plant '00-3808-01' (unpatented).

The new cultivar was selected in 2002 from a selection of the hybridization and has been asexually reproduced repeatedly by tissue culture in Bleiswijk, The Netherlands over a five-year period. The present invention has been found to retain its distinctive characteristics through successive asexual propagations.

Plant Breeder's Rights for this cultivar was granted with the European Union on May 19, 2008. 'Anthcimwi' has not been made publicly available nor sold anywhere in the world for more than one year prior to the filing of this application.

SUMMARY OF THE INVENTION

The following are the most outstanding and distinguishing characteristics of this new cultivar when grown under normal horticultural practices in Bleiswijk, The Netherlands.

1) Brown-red, durable spathes;
2) Dark-green leaves that are compact and durable;
3) Medium, long erect penducle which holds the inflorescence just above the foliage;
4) A high leaf to inflorescence ratio;
5) Rich shoot formation;
6) Compact and full plant habit;

7) Flowers early and rich and continuously throughout the year; and
8) Is a potplant, with a plant height of 30 cm to 35 cm.

DESCRIPTION OF THE PHOTOGRAPHS

This new *Anthurium* plant is illustrated by the accompanying photographs which show the overall plant habit including blooms, buds and foliage of the plant; the colors shown are as true as can be reasonably obtained by conventional photographic procedures. The photographs are of a 48-week old plant grown in a greenhouse in Bleiswijk, The Netherlands in 2007.

DESCRIPTION OF THE NEW CULTIVAR

Figure 1:
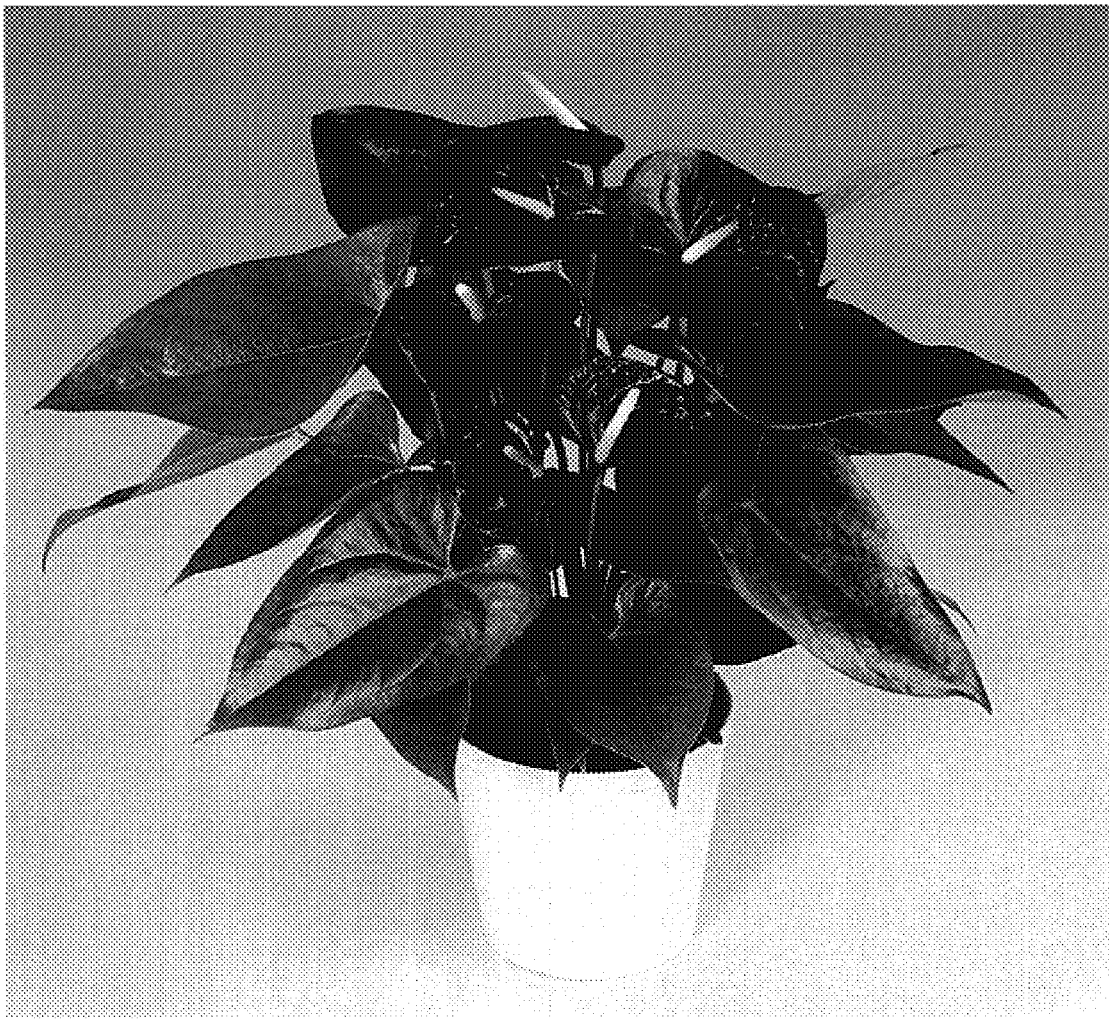
FIG. 1 shows the overall plant habit, including blooms, buds and foliage.
Figure 2:
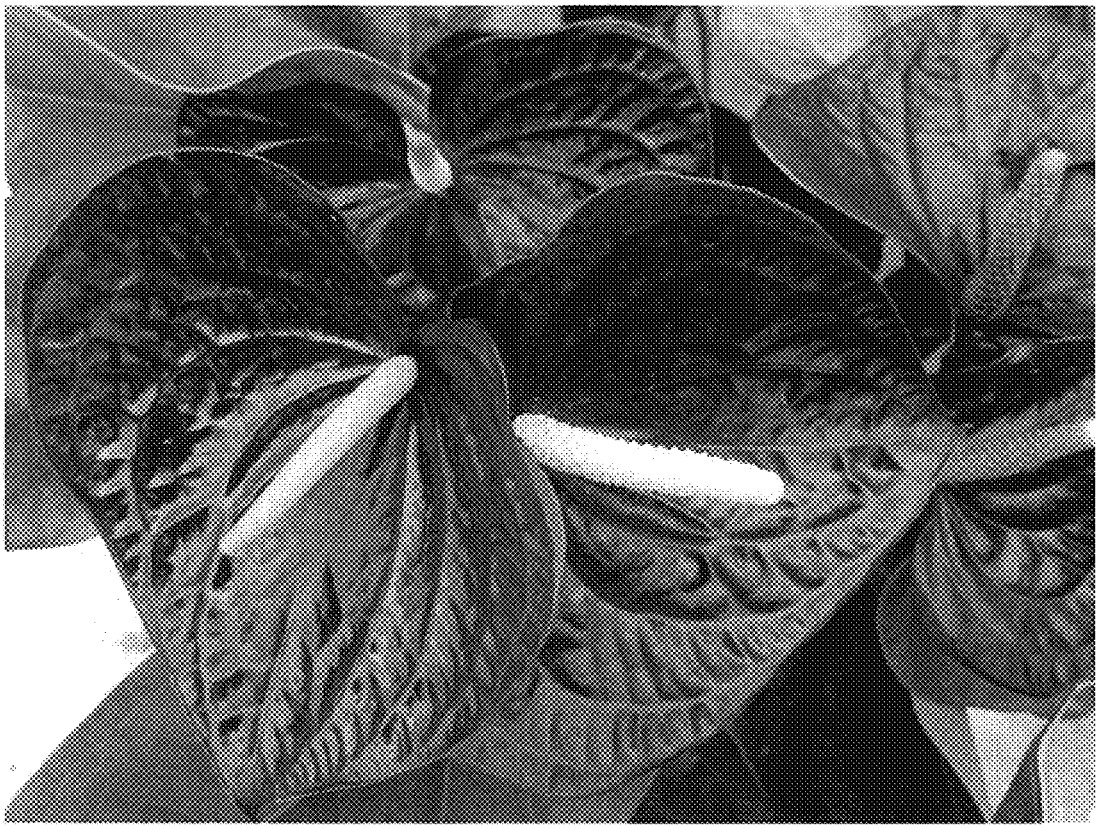
FIG. 2 shows the mature spathe.

The following detailed description sets forth the distinctive characteristics of 'Anthcimwi'. The data which define these characteristics were collected from asexual reproductions carried out in Bleiswijk, The Netherlands. The plant history was taken on 48-week old plants which were planted from tissue culture in 17-cm pots and grown in a glass greenhouse between 19° C. and 24° C. Observations were made in November of 2007. Color readings were taken under 5000 lux natural light in the greenhouse. Color references are primarily to the R.H.S. Colour Chart of The Royal Horticultural Society of London (R.H.S.) (2001).

DETAILED BOTANICAL DESCRIPTION

Classification:
*Family.*—Araceae.
*Botanical.*—*Anthurium andreanum* L.
*Common name.*—*Anthurium.*
*Cultivar name.*—'Anthcimwi'.

Parentage:

*Female parent.*—'00-2935-05', a red-flowered *Anthurium* plant (unpatented).

*Male parent.*—'00-3808-01', a brown-flowered *Anthurium* plant (unpatented).

Propagation:

*Propagation.*—Tissue culture.

*Root description.*—Fleshy-pink to cream roots with smaller hairy lateral roots; root-tips are yellow.

*Time to produce a finished flowering plant.*—45 to 50 weeks for a 17 cm pot.

Plant:

*Growth habit.*—Herbaceous perennial.

*Height (measured from soil, including inflorescence)* .—30 cm to 35 cm.

*Width (measured from leaf tips).*—35 cm to 40 cm.

Leaves:

*Immature leaves.*—Length: 6.5 cm. Width: 3.5 cm. Color Upper surface: RHS 147A with some red pigmentation in the margin. Lower surface: RHS 147B with some red pigmentation in the margin. Texture (both upper and lower surfaces): Very shiny.

*Mature leaves.*—Length (fully expanded): 20 cm to 23 cm. Width: 10 cm to 12 cm. Shape: Elliptical-cordate, weakly cupped. Apex: Acuminate. Base: Cordate. Leaf blade angle with the petiole: Between 110 degrees and 130 degrees. Leaf margin: Entire. Color: Upper surface: RHS 139A (green). Lower surface: RHS 137B (light-green). Texture (both upper and lower surfaces): Shiny, leathery and thick. Venation: Pinnate veining; the mid-vein and primary veins (the veins which radiate out from junction of petiole and leaf) protrude at the underside of the leaf blade. Venation color: Upper surface: RHS 137C (green). Lower surface: RHS 146D at leaf base and RHS 175D at the leaf tip.

*Lobes/wings.*—Arrangement: Leaf blade has two small lobes extending past the petiole. Length of lobes of mature leaf blades: 3.5 cm to 4.0 cm. Width of lobes of mature leaf blades: 4.5 cm to 5.5 cm. Distance for petiole/leaf junction to highest point on lobes of mature leaf blades: 3.5 cm to 4.0 cm. Color lobe/wing upper surface: RHS139 A. Color lobe/wing lower surface: RHS 137B.

*Petiole.*—Cross-section: Round. Diameter: 0.3 cm to 0.4 cm. Petiole length: 20 cm for a mature leaf-size. Color: Mature leaf: RHS 146A to RHS 146B. Immature leaf: RHS 164A with a light green radiance. Cataphyl color surrounding the petiole: RHS 146C (light-green) with a bit of RHS178 A (reddish) at the tip. Geniculum (A small "knee-like" structure or joint below the leaf blade that connects the leaf blade to the peduncle and only very slightly distinguishable from the petiole.): Length is 2.0 cm to 3.0 cm, width is 0.4 cm to 0.6 cm, color is approximately RHS 146D.

Inflorescence:

*Arrangement.*—Single.

*Flowering habit (length of flowering season).*—Continuous.

*Number of inflorescences per plant.*—6 to 8.

*Fragrance.*—Absent.

*Inflorescence longevity on the plant.*—Over one year.

*Inflorescence longevity as a cut flower.*—Approximately 22 days.

Spathe:

*Buds.*—The spathe is tightly rolled around the spadix and extrudes from the peduncle sheath. After the spathe is fully opened the peduncle elongates some extra centimeters.

*Arrangement.*—Spathe angle with the peduncle is between 100 degrees and 110 degrees; the spathe stands on a slightly curved wiry peduncle about 5 cm to 8 cm above the foliage.

*Shape.*—Cordate, when fully-opened cupped to some degree.

*Apex.*—Mucronate tip.

*Base.*—Cordate.

*Margin.*—Smooth (entire).

*Texture.*—Blistered.

*Size.*—Height: 25 cm to 30 cm (Peduncle length). Length: 9 cm to 11 cm. Width: 11 cm to 13 cm.

*Color.*—Just fully open: Upper surface: RHS 187A (brown-red). Lower surface: RHS 187B (brown). 7 to 8 weeks after opening: Slightly darker than RHS 187A (brown). 14 to 16 weeks after opening: Slightly darker than RHS 187A (brown).

Peduncle:

*Shape.*—Erect.

*Cross-section.*—Round.

*Length.*—25 cm to 30 cm.

*Diameter.*—0.3 cm to 0.5 cm.

*Color.*—With dark green RHS 147A and brown RHS 166A.

Flowering time:

*General.*—One small rooted untreated tissue culture plant of 2 cm tall will flower, depending on season and after 9 to 10 months 2 to 3 blossoms appear. More blossoms appear after some additional weeks so that a full flowering and commercial plant will have 6 to 9 brown-red spathes. Smaller blossoms may occur on less mature growth.

Spadix:

*Size.*—Length: 4 cm to 6 cm (depending on flower size). Width (at apex): 0.5 cm to 0.6 cm. Width (at base): 0.6 cm to 0.8 cm.

*Shape.*—Columnar.

*Apex.*—Rounded.

*Base.*—Truncate.

*Margin.*—Entire.

*Color.*—Immature: RHS 153A (green-yellow). Mature: RHS 158A (white). Ages to: RHS 144A (green).

Flowers:

*Quantity per spadix.*—150 to 250.

*Spadix flower arrangement.*—Bisexual, rounded in cross-section.

*Shape.*—Rounded.

*Size.*—Length: 0.1 cm to 0.2 cm. Diameter (max): 0.2 cm.

*Color.*—RHS 155B (white).

Reproductive organs:

*Stamens.*—Not visible.

*Pollen.*—Abundant.

*Pollen color.*—RHS 156D (white).

*Pistil.*—Quantity: Many. Length: Less than 0.01 cm. Color: RHS 156D.

*Style.*—Not observed.

*Stigma.*—Shape: Ovoid. Diameter: Less than 0.01 cm. Color: RHS 155D (white).

*Ovary.*—Rarely visible.

*Ovary color.*—RHS 155D (white).

Fruit and seed set: Seed production has not been observed to date.

Disease and insect resistance: No particular resistance or susceptibility that is different from other *Anthurium* varieties.

COMPARISON WITH PARENTAL AND COMMERCIAL CULTIVARS

'Anthcimwi' differs from the female parent '00-2935-05' (unpatented), by having brown-red spathes, while '00-2935-05' has red spathes. In addition, 'Anthcimwi' has a more compact plant habit than '00-2935-05'.

'Anthcimwi' differs from the male parent '00-3808-01' (unpatented), in that 'Anthcimwi' has brown-red spathes, while '00-3808-01' has brown spathes.

'Anthcimwi' is similar to the commercial variety 'Anthbrabon' (unpatented; registered on Oct. 22, 2007 number EU 21088), however, there are differences as listed in Table 1 below:

TABLE 1

Comparison of characteristics between 'Anthcimwi' and 'Anthbrabon'

| Characteristic | 'Anthcimwi' | 'Anthbrabon' |
|---|---|---|
| Spathe shape | Cordate, cupped | Oblong-cordate, not cupped |
| Spathe color (upper surface, just fully opened) | RHS 187A | RHS 53A |
| Spadix length | 4 cm to 6 cm | 3 cm to 5 cm |
| Spadix width | 0.5 cm to 0.6 cm | 0.9 cm to 1.0 cm |
| Petiole length | 20 cm | 25 cm |
| Petiole color (mature leaf) | RHS 146A to RHS 146B | RHS 144A |

I claim:

1. A new and distinct cultivar of *Anthurium* plant, named 'Anthcimwi', as shown and described herein.

* * * * *